(12) United States Patent
Cinelli et al.

(10) Patent No.: US 6,710,099 B2
(45) Date of Patent: Mar. 23, 2004

(54) DISPOSABLE ABSORBENT ARTICLES WITH IMPROVED ADHESIVE FOR ATTACHMENT TO THE SKIN TO FACILITATE WATER ADHESION STABILITY WITH LOW PAIN LEVEL REMOVAL

(75) Inventors: Fabio Cinelli, Bologna (IT); Antonello Colaianni, Pescara (IT); Adelia Alessandra Tordone, Pescara (IT); Hugh Semple Munro, Chipping Camden (GB); Brian John Tighe, Birmingham (GB)

(73) Assignee: The Procter & Gamble Company, Cincinnati, OH (US)

( * ) Notice: Subject to any disclaimer, the term of this patent is extended or adjusted under 35 U.S.C. 154(b) by 29 days.

(21) Appl. No.: 09/917,469

(22) Filed: Jul. 27, 2001

(65) Prior Publication Data

US 2002/0013565 A1 Jan. 31, 2002

Related U.S. Application Data

(63) Continuation of application No. PCT/US00/02706, filed on Feb. 2, 2000.

(30) Foreign Application Priority Data

Feb. 2, 1999 (EP) .............................. 99102048

(51) Int. Cl.$^7$ ................................. C08L 15/00
(52) U.S. Cl. ...................... 523/111; 523/105
(58) Field of Search ................. 523/105, 111

(56) References Cited

U.S. PATENT DOCUMENTS

| | | |
|---|---|---|
| 3,577,989 A | 5/1971 | Anderson |
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,609,518 A | 9/1986 | Curro et al. |
| 4,629,643 A | 12/1986 | Curro et al. |
| 4,699,146 A | 10/1987 | Sieverding |
| 4,784,656 A | 11/1988 | Christian |
| 5,006,394 A | 4/1991 | Baird |
| 5,015,244 A | 5/1991 | Cross |
| 5,173,302 A | 12/1992 | Holmblad et al. |
| 5,356,963 A * | 10/1994 | Kauffman et al. ............ 524/43 |
| H1602 H | 10/1996 | Brock |
| 5,670,557 A | 9/1997 | Dietz et al. |
| 5,728,146 A | 3/1998 | Burkett et al. |
| 5,741,318 A | 4/1998 | Ouellette et al. |
| 6,191,189 B1 * | 2/2001 | Cinelli et al. ............... 523/111 |
| 6,197,845 B1 * | 3/2001 | Janssen et al. .............. 523/111 |
| 6,198,017 B1 | 3/2001 | Basedow et al. |
| 6,211,263 B1 * | 4/2001 | Cinelli et al. ............... 523/111 |
| 6,264,642 B1 * | 7/2001 | Kauen et al. .......... 604/385.28 |
| 6,277,106 B1 * | 8/2001 | Boudry et al. ............... 604/394 |
| 6,316,524 B1 * | 11/2001 | Corzani et al. ............. 523/111 |
| 6,322,801 B1 * | 11/2001 | Lorenzi et al. ............. 424/405 |
| 6,365,645 B1 * | 4/2002 | Cinelli et al. ............... 523/105 |
| 6,369,126 B1 * | 4/2002 | Cinelli et al. ............... 523/105 |
| 6,413,247 B1 * | 7/2002 | Carlucci et al. ....... 604/385.01 |
| 6,417,424 B1 * | 7/2002 | Bewick-Sonnotag et al. .... 604/367 |

FOREIGN PATENT DOCUMENTS

| | | |
|---|---|---|
| CH | 643730 A1 | 11/1980 |
| EP | 245064 A2 | 11/1987 |
| EP | 184470 B1 | 4/1991 |
| EP | 554106 A1 | 8/1993 |
| EP | 753290 A2 | 1/1997 |
| EP | 638303 B1 | 11/1997 |
| EP | 850625 A1 | 7/1998 |
| EP | 850649 A1 | 7/1998 |
| EP | 855190 A1 | 7/1998 |
| EP | 676457 B1 | 10/1998 |
| EP | 888786 A2 | 1/1999 |
| GB | 1078588 | 5/1966 |
| GB | 2115431 A1 | 9/1983 |
| GB | 2152387 A1 | 8/1985 |
| WO | WO 93/09744 A1 | 5/1993 |
| WO | WO 93/10201 A1 | 5/1993 |
| WO | WO 93/11725 A1 | 6/1993 |
| WO | WO 93/11726 A1 | 6/1993 |
| WO | WO 95/16424 A1 | 6/1995 |
| WO | WO 95/20634 A1 | 8/1995 |
| WO | WO 96/13238 A1 | 5/1996 |
| WO | WO 96/33683 A1 | 10/1996 |
| WO | WO 97/01311 A1 | 1/1997 |
| WO | WO 97/05171 A1 | 2/1997 |
| WO | WO 97/24149 A1 | 7/1997 |
| WO | WO 97/49361 A1 | 12/1997 |
| WO | WO 98/03208 A1 | 1/1998 |
| WO | WO 98/28017 A1 | 7/1998 |
| WO | WO 99/00092 A1 | 1/1999 |
| WO | WO 00/45766 A1 | 8/2000 |
| WO | WO 00/45863 A1 | 8/2000 |
| WO | WO 00/45865 A1 | 8/2000 |
| WO | WO 00/45866 A1 | 8/2000 |

* cited by examiner

*Primary Examiner*—Edward J. Cain
*Assistant Examiner*—Katarzyna Wyrozebski Lee
(74) *Attorney, Agent, or Firm*—Peter D. Meyer

(57) ABSTRACT

The present invention relates to a disposable absorbent articles such as diapers and sanitary napkins which are provided with adhesives for attachment of the article to the skin. In particular the present invention relates to adhesives which provide secure attachment and are pleasing to the skin upon application, yet cause no discomfort upon removal. In particular the present invention relates to an adhesive which provide secure attachment under moist and wet skin conditions and which maintains adhesive peel strength even under exposure to excess water.

21 Claims, No Drawings

DISPOSABLE ABSORBENT ARTICLES WITH IMPROVED ADHESIVE FOR ATTACHMENT TO THE SKIN TO FACILITATE WATER ADHESION STABILITY WITH LOW PAIN LEVEL REMOVAL

PRIOR APPLICATION

This application is a continuation of PCT Application No. PCT/US00/02706 filed on Feb. 2, 2000 and published in English, which claims priority to EP Application No. 99102048, filed on Feb. 2, 1999.

FIELD OF THE INVENTION

The present invention relates to a disposable absorbent articles such as diapers, sanitary napkins, pantiliners, tampons, perspiration pads, adult incontinence devices and the like to be attached directly to the skin of the wearer. The articles utilise an improved adhesive so as to facilitate easy application and removal of the article from the wearer, whilst ensuring maintenance of the article in the desired position. In particular the adhesives provide attachment on moist and wet skin for the entire period of wear, including circumstances or periods of wear during which the adhesive is exposed to excess amounts of liquids.

BACKGROUND OF THE INVENTION

The present invention relates to adhesives which are particularly useful to absorbent articles for absorption of body liquids which naturally emanate from a body without a wound. For example to attach sanitary napkins or pantiliners in the genital region. Also incontinence devices which are worn e.g. in the genital region or perspiration pads which are worn in the arm pit region of a person can suitably employ the adhesive of the present invention.

Such adhesives have been generally disclosed in for example U.S. statutory invention registration H1602 or WO 96/33683 and WO 95/16424. The latter discloses sanitary articles having a topical adhesive which is applied on the wearer facing side of a sanitary napkin along the entire periphery. WO 96/13238 discloses a topical adhesive which is described in terms of frequency dependency. EP-638 303 discloses the use of a topical adhesive on side cuffs of sanitary napkins in order to keep the cuffs in an upright position. Swiss publication CH-643730 discloses the use of a very long sanitary napkin having chamfered outer edges with a topical adhesive at the four corners of the outer edges in order to provide a topical adhesive area well outside the region of pubic hair growth.

However all of these disclosures typically disclose a product which is designed to be utilised in combination with an undergarment and hence the degree of adhesion actually provided is very low and is not designed to withstand any excessive pressure. Moreover the adhesive is only discussed in general terms or concentrates on the area of application of the adhesive to the article. The nature of adhesive per se other than the basic physical requirements such as pressure sensitivity are not discussed in particular with reference to the chemical composition or the adhesive criteria.

The prior art in the general field of adhesives for attachment to the skin is particularly developed in the field of articles such as band-aids, plasters and bandages. These articles are however typically applied in an emergency situation, where for example, a cut into the skin of the wearer has occurred and absorption of the body liquids emanating from a wound is desired. In this context performance aspects of the article such as easy application and use of the product, comfortable wear as well as painless removal, and discreteness are again subordinate, to other criteria in this case such as sterility, healing support, and mechanical protection of the wound. Also such wound covering absorbent articles are mostly adhered to the skin where prior to application of the absorbent article bodily hair can be removed or where little hair grows.

In order to provide the desired level of adhesion of such bandages, the prior art typically discloses the utilisation of certain adhesives having very high cohesive strengths such as rubber based adhesives and acrylics. These adhesives are then applied as thick layers to maximise the adhesive force by which the bandage is secured to the skin of the wearer.

U.S. Pat. No. 4,699,146 discloses hydrophilic elastomeric pressure sensitive adhesives suitable for use with ostomy devices, bandages, ulcer pads, sanitary napkins, diapers, and althetic padding. The adhesive comprises at least 1 uradiation cross linked organic polymer and an adhesive plasticizer.

GB 2 115 431 discloses adhesives for bandages, wounds or burn dressings, EKG adhesives, sanitary napkins, diapers and ulcer pads. The adhesive comprises an uradiation cross-linked organic polymer such as polyvinylpyrrolodine and an adhesive plasticizer.

However, for application such as absorbent articles it is important that the adhesive has a skin compatible composition and not be harsh or aggressive towards the skin or cause skin irritation or inflammation. Also it is preferred if the adhesive is compliant with the skin of the wearer such that maximum skin surface contact between the adhesive and the skin is achieved. Moreover, it is also desirable to provide an adhesive such that the absorbent article can be readily removed from the wearer, without the wearer experiencing any unacceptable pain level. This is particularly important under circumstances, where the article is removed and reapplication of the article once or even a number of times is required for example to allow for urination and or to ensure the application of such articles on sensitive skin and wearer groups such as infants. However, on the other hand the desired level of adhesion, albeit painless should of course also be maintained during such multiple applications of the article.

The problem of achieving the desired adhesion level is further exacerbated under wet skin conditions. Typically, prior to the placement of the article the skin is cleaned and is usually as a result moist. The currently available adhesives, such as hydrocolloids, however often do not immediately strongly adhere to the skin and may need to be held in place until sufficient minimum adhesion occurs. Moreover, the overall adhesive ability of such adhesives tends to be significantly reduced on wet skin surfaces per se, so that the article will typically not remain attached to the skin during wearer if any pressure is exerted onto the article, for example by the movement of the wearer.

Moist and wet skin however is not just a problem which is prevalent at the article application stage as a significant amount of moisture is also generated during the use of the article from the wearer by perspiration and from bodily fluids. Under such circumstances currently available adhesives typically cannot absorb this moisture and again the adhesive strength is reduced to such an extent that the article will often become detached under exertion of pressure during wear. It is hence very important to provide an adhesive which provides both initial adhesion and maintenance of its adhesive strength on wet skin. Moreover, it is also another important factor for the product performance that the adhesive is also stable to exposure to excess quantities of liquid such as water, urine and menstrual fluids and will also not loose its adhesive strength under such circumstances.

None of the prior art in the field of absorbent articles however even recognises or addresses the problem of providing these articles with an adhesive which meets these criteria, in particular adhesives which adhere to wet skin and are stable and maintain their adhesiveness even when exposed to excessive amounts of liquid.

Adhesion to wet skin is addressed for example in WO 98/03208 which discloses medical pressure sensitive adhesives which can adhere to dry or wet skin and which comprise a mixture of hydrophilic (meth)acrylate copolymer containing tertiaryamino groups, a hydrophilic (meth)acrylate copolymer containing carboxyl groups, carboxylic acids and a crosslinking system. However this document does not discuss adhesion after exposure to excess liquid.

Hence there still exists a need to disposable absorbent articles having an adhesive for the secure attachment and painless removal of the article from the skin suitable for use of sensitive skin of an infant and or of the genitalia and it is thus an object of the present invention to provide such an article.

It is another objective of the present invention to provide an adhesive that exhibits an ability to adhere to skin upon reapplication, particularly multiple reapplication for example when the article is removed for urination purposes or is misplaced, whilst still allowing painless removal.

It is yet a further objective of the present invention that the adhesive will adhere to moist or wet skin, independent of whether this is direct application of the article onto wet skin, or moisture which is generated on the skin surface during the wearing period of the article. In particular it is an objective of the present invention to provide an adhesive which is liquid stable particularly to water and urine, such that the adhesion properties will not be significantly effected in the presence thereof over the period of wear of the article.

It is another object of the present invention to provide an adhesive which upon removal from the skin of the wearer leaves no residues. It is yet another object of the present invention to provide an adhesive which does not cause a cold or otherwise unacceptable temperature sensation upon application to the wearer.

An additional object of the present invention to provide an adhesive which provides flexibility, stretchability and contractability so that it is able to adapt to the contours of the body during all bodily movements and hence be comfortable for the wearer of the article, whilst still having sufficient adhesive capacity to ensure secure attachment during use.

It has now been surprisingly found that the above drawbacks will be substantially alleviated by providing the absorbent article with an adhesive as defined hereinafter. The adhesive provides secure attachment, is pleasing to the skin upon application, and yet causes no discomfort upon removal and maintains its adhesive strength over the period of wear even under exposure to excess liquids.

SUMMARY OF THE INVENTION

Any disposable absorbent article known in the art can be provided with the adhesive according to the present invention. According to the present invention the adhesive is provided so as to have an initial peel strength ($P_I$) under normal ambient conditions and a final peel strength ($P_F$) after exposure to water according to the test method described herein, whereby the ratio of $P_I$ to $P_F$ is from 2:1 to 2:4 preferably from 2:1.25 to 2:2.5 and has a water absorption capacity as defined in the test herein of at least 3% by weight of said adhesive.

The adhesive allows attachment of disposal absorbent articles to the skin of the wearer, the adhesive being provided as a layer having a certain thickness or calliper C measured in millimeters (mm), typically on at least part of the wearer facing surface of the article.

Detailed analysis of the sequence of common situations occurring from the application of absorbent articles to the time of removal of such articles has shown that specific adhesive characteristics need to be preferably satisfied in order to achieve the desired performance objectives, in particular to secure initial attachment, secure attachment during use and painless removal after wear. The characteristics which have been considered in this context are the elastic modulus describing the elastic behaviour of the material and the viscous modulus which describes the viscous behaviour of the adhesive material.

The viscous behaviour of the adhesive can be interpreted to represent an indication of the ability of the adhesive to quickly attach and securely adhere to a particular surface. The elastic behaviour can be interpreted as an indication of the "hardness" behaviour of the adhesive. Its value is also important for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

In order to provide adhesives for secure initial and prolonged attachment and easy/painless removal the relation between the elastic modulus and the viscous modulus as well as their dynamic behaviour is also of importance.

The adhesive has an elastic modulus at a temperature of 37° C. (100° Fahrenheit) abbreviated $G'_{37}$, a viscous modulus at a temperature of 37° C. (100° Fahrenheit) of $G''_{37}$, and a viscous modulus at a temperature of 25° C. (77° Fahrenheit) of $G''_{25}$.

The adhesive according to the present invention preferably satisfies the following conditions;

| | |
|---|---|
| $G'_{37}$ (1 rad/sec) | is in the range 500 Pa to 20000 Pa, preferably 700 Pa to 15000 Pa, most preferably 1000 Pa to 10000 Pa. |
| $G''_{37}$ (1 rad/sec) | is in the range 100 Pa to 15000 Pa, preferably 100 Pa to 10000 Pa, most preferably 300 Pa to 5000 Pa. |
| and the ratio of $G'_{37}$ (1 rad/sec)/ $G''_{37}$ (1 rad/sec) | is in the range of 1 to 30. |

Provided the above rheological conditions are satisfied the adhesives will also satisfy conditions such as sufficient cohesiveness (to prevent residue of adhesive on the skin) which are important for commercial use of such adhesives and apparent to those skilled in the art. Adhesive compositions which satisfy the above criteria can be used as adhesives for the article provided they also satisfy the common requirements of being safe for use on human or animal skin during use and generally after disposal of the article.

Often the criteria of hygienic appearance such that adhesive compositions which are transparent or white upon application are preferred.

It has been determined that the relation between the thickness or calliper C, measured in millimeters (mm), of the layer in which the adhesive is provided, typically onto at least a portion of the wearer facing surface of the article, and the viscous modulus $G''_{25}$ at about 100 rad/sec of the adhesive, is relevant to the scope of providing an easy and painless removal from the wearer's skin of such a adhesive applied on at least a portion of the wearer facing surface of an absorbent article for attachment of said article to the skin of a wearer.

The adhesive of the present invention is thus preferably provided as a layer having a thickness C such that the viscous modulus $G''_{25}$ (100 rad/sec) and the thickness C preferably satisfy the following empirical equation:

$$G''_{25} \leq [(7.00+C) \times 3000] \text{ Pa}$$

and preferably also the following empirical equation:

$$G''_{25} \leq [(5.50+C) \times 1700] \text{ Pa}$$

DETAILED DESCRIPTION OF THE INVENTION

According to the present invention the adhesive can be utilised on disposable absorbent articles such as diapers, sanitary napkins, panty liners, incontinence devices, perspiration pads and tampons. The word "skin" according to the present invention does not only relate to the specific derma of the user but includes the mucous tissue as well as the hair which is typically found in the genital region.

Due to the nature and environment in which such disposable absorbent articles are utilised it is an essential feature that the adhesive has a water absorption capacity as defined in the test herein of at least 3% by weight of said adhesive (so that the adhesive adheres directly onto wet or moist skin). In addition it is also essential that the adhesive maintain its adhesive strength in the presence of excess liquid. In particular, the ratio of the peel strength of the adhesive as determined in the test methods herein should most preferably be maintained at a constant value such that the ratio of initial peel strength ($P_I$) and the final peel strength ($P_F$) is from 2.0:1 to 2:4, preferably from 2:1.25 to 2:2.50, most preferably from 2.0:1.5 to 2.0:2.5. Typically for disposable absorbent articles the initial peel strength for dry and more preferably also for wet skin should be from 0.1N/cm to 5.0N/cm, preferably from 0.5N/cm to 3.0N/cm.

It is further also preferable that the adhesive in addition to maintaining its peel strength over a period of time even in the presence of water also absorbs less than 15%, preferably less than 10%, more preferably less than 7% water. Whilst not intending to being bound by theory, it is believed that in order to obtain direct adhesion onto wet skin and maintain constant adhesion performance over a period of wear, even when exposed to excess liquids or high humidity the ability of the adhesive to absorb water needs to be considered. In particular, it has been identified that, not only the absolute ability of the adhesive needs to be considered, but also the rate of water absorption in order to provide an adhesive meeting the above identified performance parameters.

For example hydrocolloid adhesives which are known in the art comprising a 3-dimensional rubber matrix and colloidal absorbent particles dispersed therein are only able to absorb limited amounts of water through the colloidal particles themselves and not the matrix itself. In addition the rate at which water is absorbent is slow. Hence these prior art adhesives do not adhere to wet surfaces.

Prior art hydrogel adhesives on the other hand are able to not only absorb large quantities of water but also at a very fast rate. As a result such adhesives may be able to adhere, to wet surfaces, however due to the combination of fast rate of absorption and large absolute water uptake, these adhesives loose their adhesive strength rapidly in the presence of excess water or high humidity.

Accordingly the adhesives of the present invention exhibit both an ability to adhere directly to wet skin, by having a minimum absolute water absorption ability in combination with a rate of absorption such that the peel strength remains within defined levels over the period of wear.

The adhesive is provided with the preferred pattern, typically on the wearer facing surface of the article, as a layer having a thickness or calliper C that is preferably constant. The layer can be preferably continuous or alternatively discontinuous, e.g. in form of dots, spirals, or stripes.

Even though adhesives are used like pressure sensitive adhesives on human skin hair and mucous tissues, it is understood that the topical adhesive compositions could only with difficulty be considered typical pressure sensitive adhesives (referred to as PSA hereinafter) on the basis of the most characteristic rheological behaviours identifying such materials.

In fact as the person skilled in the art of adhesives knows, the most characteristic feature that distinguishes a PSA from other substances that can temporarily adhere objects (e.g. water between two glass plates could) is the fact that their rheological parameters and especially the Elastic Modulus G' vary greatly with the frequency of applied stresses. More in particular, G' of PSA can increase over some orders of magnitude, while the frequency of applied stresses varies from typical bonding frequency to typical debonding frequency, i.e. 1 rad/s to 100 rad/s as indicated below.

As a first consequence, it is therefore inadmissible to define materials intended for use as "adhesives" by giving values of rheological parameters and especially of G' at a fixed value of frequency. This can be misleading because in the absence of other characteristics it will include materials which have no practical value. It is hence necessary that rheological characterisation must be on the basis of dynamic considerations. This not only applies to the Elastic Modulus G' but also to the viscous modulus G" and hence also for tan (d)=G"/G'.

It is well known that typical PSAs have not only a high variation of G' across the considered frequencies, but also that there is an even higher variation of G" which can get close or become even higher than the value of G', i.e. tan (d) becomes about or even greater than 1, in particular at the frequencies that are typical of debonding.

Without wishing to be bound by theory this can be interpreted as meaning that a high fraction of the energy applied for the debonding is dissipated within the adhesive (so it is not effective in causing the debonding) and through the interface of the adhesive and the skin, while this fact causes macroscopically the recording of a very high level of adhesive force.

As indicated above materials useful as adhesives according to the present invention have Theological characteristics which are measured at a reference temperature of 37° C. (as usual body temperature of humans) and in a range of frequencies. It has been found that upon application of a disposable absorbent article with a adhesive the adhesive contact is formed at a low frequency, while debonding happens at the speed of removing the article. This speed is expressed as a frequency of 100 rad/s, while the low frequency of forming the adhesive bond has been found to be on the order of 1 rad/s. Therefore, the frequency range for use according to the present invention is between 1 and 100 rad/s.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion while the material remains soft and capable of gently adhering to skin.

The ratio of $G'_{37}$ (1 rad/sec) over $G''_{37}$ (1 rad/sec) is important to ensure that these two values are balanced upon adhesion to the skin.
Importantly, the ratio of $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

needs to be large enough to ensure that the dynamic behaviour of both the elastic and the viscous module are maintained in a relationship which provides secure adhesion and painless and easy removal.

Finally the person skilled in the art will also recognise that the Glass Transition Temperature Tg of the adhesive composition, the specific heat capacity, and the specific heat conductivity are parameters which are useful to more fully define the group of useful adhesives.

The following set of characteristics should preferably be satisfied for the adhesive of the present invention:

| | |
|---|---|
| $G'_{37}$(1 rad/sec) | is in the range 500 Pa to 20000 Pa, preferably 700 Pa to 15000 Pa, most preferably 1000 Pa to 10000 Pa. |
| $G''_{37}$(1 rad/sec) | is in the range 100 Pa to 15000 Pa, preferably 100 Pa to 10000 Pa, most preferably 300 Pa to 5000 Pa. |
| the ratio of $G'_{37}$(1 rad/sec)/$G''_{37}$(1 rad/sec) is in the range of 1 to 30. | |
| the ratio $\dfrac{G'_{37}(100 \text{ rad/sec}) - G''_{37}(100 \text{ rad/sec})}{G'_{37}(1 \text{ rad/sec}) - G''_{37}(1 \text{ rad/sec})}$ is not less than 0.5, preferably in the range 0.7 to 3, most preferably in the range 1 to 1.8. | |

The value of the ratio of $G'_{37}/G''_{37}$ at least for the frequency range above 1 rads/up to 100 rads/s should preferably be not less than 0.5, preferably from 0.7 to 10 and most preferably from 1 to 7.

The rheological behaviour can also be related to the values of the Glass Transition Temperature Tg. For topical adhesives according to the present invention Tg should preferably be less than 0° C., more preferably less than −5° C. and most preferably less than −10° C.

In order to provide adhesive compositions which satisfy the requirements of the above rheological and physical characteristics of an adhesive any medically suitable substantially water insoluble pressure sensitive adhesives comprising a polymer which forms a 3-dimensional matrix meeting the these characteristics may be utilised.

According to the present invention the 3 dimensional matrix also referred to herein as a gel, comprise as an essential component, a polymer which can be physically or chemically cross linked. The polymer may be naturally or synthetically derived. The uncrosslinked polymer includes repeating units or monomers derived from vinyl alcohols, vinyl ethers and their copolymers, carboxy vinyl monomer, vinyl ester monomers, esters of carboxy vinyl monomers, vinyl amide monomers, anionic vinyl monomers, hydroxy vinyl monomers, cationic vinyl monomers containing amines or quaternary groups, N-vinyl lactam monomer, polyethylene oxides, polyvinylpyrrolidone (PVP), polyurethanes, acrylics such as methyl acrylate, 2-hydroxyethyl methacrylate, methoxydiethoxyethyl methacrylate and hydroxydiethoxyethyl methacrylate, acrylamides, and sulphonated polymers such as acrylamide sulphonated polymers for example 2 acrylamido methylpropane sulphonic acid and acrylic (3-sulphopropyl) ester acid, and mixtures thereof. Also acrylonitrile, methacrylamide, N,N,-dimethylacrylamide, acrylic esters such as methyl, ethyl and butyl acrylates. Alternatively, the uncrosslinked polymer may be a homopolymer or copolymer of a polyvinyl ether, or a copolymer derived from a half ester of maleic ester. Similarly any other compatible polymer monomer units may be used as copolymers such as for example polyvinyl alcohol and polyacrylic acid or ethylene and vinyl acetate.

As another alternative, the polymers may be block copolymer thermoplastic elastomers such as ABA block copolymers such as styrene-olefin-styrene block copolymers or ethylene-propylene block copolymers. More preferably such polymers include hydrogenated grade styrol/ethylene-butylene/styrol (SEBS), styrene/isoprene/styrene (SIS), and styrol/ethylene-propylene/styrol (SEPS).

Particularly preferred polymers are acrylics, sulphonated polymers such as acrylamide sulphonated polymers, vinyl alcohols, vinyl pyrrolidone, polyethylene oxide and mixtures thereof. Most preferred are nitrogen containing polymers.

According to the present invention the 3 dimensional adhesive matrix also essentially comprises a plasticiser, which is preferably a liquid at room temperature. This material is selected such that the polymer may be solubilized or dispersed within the plasticiser. For embodiments wherein irradiation cross linking is to be carried out, the plasticiser must also be irradiation cross linking compatible such that it does not inhibit the irradiation cross linking process of the polymer. The plasticiser may be hydrophilic or hydrophobic.

Suitable plasticisers include water, alcohols, polyhydric alcohols such as glycerol and sorbitol, and glycols and ether glycols such as mono- or diethers of polyalkylene gylcol, mono- or diester polyalkylene glycols, polyethylene glycols (typically up to a molecular weight of about 600), glycolates, glycerol, sorbitan esters, esters of citric and tartaric acid, imidazoline derived amphoteric surfactants, lactams, amides, polyamides, quaternary ammonium compounds, esters such phthalates, adipates, stearates, palmitates, sebacates, or myristates, and combinations thereof. Particularly preferred are polyhydric alcohols, polyethylene glycol (with a molecular weight up to about 600), glycerol, sorbitol, water and mixtures thereof.

Typically the adhesive comprises a ratio of polymer to plasticiser by weight of from 1:100 to 100:1, more preferably from 50:1 to 1:50. However, the exact amounts and ratios of the polymer and plasticiser will depend to a large extent on the exact nature of polymer and plasticisers utilised and can be readily selected by the skilled person in the art. For example a high molecular weight polymer material will require a greater amount of plasticiser than a low molecular weight polymer.

Other common additives known in the art such as preservatives, antioxidants, pigments, mineral fillers and mixtures thereof may also be comprised within the adhesive composition in quantities up to 10% by weight each respectively.

According to the present invention the polymer component of the adhesive can be physically or chemically cross-linked in order to form the 3 dimensional matrix. Physical cross linking refers to polymers having cross links which are not chemical covalent bonds but are of a physical nature such that there are areas in the 3 dimensional matrix having high crystallinity or areas having a high glass transition temperature. Chemical cross-linking refers to polymers which are linked chemical bonds. Preferably the polymer is chemically cross-linked by radiation techniques such as thermal-, E beam-, UV-, gamma or micro-wave radiation. Preferably, the polymer comprises less than 10% hydrocolloid particles by weight of the adhesive, and more preferably the polymer comprises less than 5% hydrocolloid particles by weight of the adhesive.

In addition when chemical crosslinks are formed in the system, a polyfunctional cross linker and/or a free radical initiator may be present in the premix to initiate the crosslinking upon irradiation. Such an initiator can be present in quantities up to 5% by weight, preferably from 0.02% to 2%, more preferably from 0.02% to 0.2%. Suitable photoinitiators include type I-α-hydroxy-betones and benzilidimethyl-betols e.g. Irgocure 651 which are believed to on irradiation to form benzoyl radicals that initiate polymerization. Particularly preferred is I-hydroxycyclohexylphenylketone (available under the trade name Irgacure 184 from Ciba Speciality Chemicals). In addition from 0.02% to 2% of thermal initiators may also be used.

The resulting adhesive compositions are mainly hydrophilic. Hydrophobic and mixed phase compositions are dependant upon the nature of the components of the adhesive. In addition a mixture of monomers whether hydrophilic or both hydrophobic and hydrophilic may result in a single phase or mixed phase of at least 2 phases. Preferably, the adhesives of the present invention are mixed phase hydrophilic hydrophobic.

A mixture of monomers which may result in 1, 2 or more phases are preferred. Mixed phase adhesives are compositions in which both hydrophobic and hydrophilic components, preferably in both plasticisers and polymers, form two or more separate phases. In such cases an emulsifier is preferably present at a suitable level to form stable emulsions between the incompatible phases.

Whilst not intending to be bound by theory it is believed that the improved peel strength liquid stability particularly with respect to water of the adhesives is obtained from a monomer mix comprising both hydrophilic e.g. polar and/or ionic monomers preferably anionic water soluble monomer and hydrophobic i.e nonionic monomers. Preferably the ratio of hydrophilic monomers to hydrophobic monomers should be in the range of from 5:1 to 1:5 and preferably from 3:1 to 1:3, preferably from 2:1 to 1:2. The hydrophilicity and hydrophobicity of a monomer component is always relative to the other component. Typically prior art hydrogel adhesives comprise hydrophilic monomers only, as a consequence of which they have a high rate of water absorption and do not maintain adhesion after exposure to excess liquid. Whilst not intending to be bound by theory, it is believed that the presence of a hydrophobic component in the adhesive matrix reduces the rate of absorption of water of the adhesive. As a result the distribution of the water absorbed by the adhesive is more uniform. Consequently a water film is not generated between the surface of the skin and the adhesive, which if present, prevents the formation of bonds between skin and adhesive and thus the adhesive capacity of the adhesive itself.

Thus the invention seeks to provide a homogeneously dispersed reaction mixture comprising both hydrophobic and hydrophilic components which, on polymerisation separates into a biphasic or a multiphasic structure. The phases have in some cases been observed to have a thickness of about 100 microns +/−50 microns. The reaction mixture may contain one or more surface active agents which may assist or promote phase separation but in the course of polymersation become anistropically distributed between the result phases.

The presence of a hydrophobic monomer or polymer may be necessary in the initial homogenous dispersion in order to more effectively promote phase separation.

Suitable preferred hydrophilic monomers are acrylic acid, and salts thereof, 2-acrylamido methylpropane sulphonic acid, acrylic (3-sulphopropyl) ester acid and salts thereof and combinations thereof. Suitable hydrophobic monomer components are acrylamide, acrylonitrile, methyl-, ethyl-, butyl hexyl, iso octyl- and isodecyl acrylates and methacrylate, vinyl ethers, vinyl pyrrolidine, gylcidyl acrylate and 2-hydroxyethyl acrylate, tehra-hydrofurfuryl acrylate, hydroxypropyl acrylate, vinyl propionate and vinyl butyrate, and combinations thereof. Particularly preferred are ethoxy ethyl acrylate or butyl acrylate.

When the adhesive comprises a hydrophobic component, such as butyl acrylate as well as a hydrophilic monomer (i.e. the aforesaid water soluble ionic monomer), such as NaAMPS, the nonionic water soluble monomer, for example NNDMA, acts as a so-called "reactive solvent bridge" to provide intimate mixing of the various seemingly incompatible components of the reaction mixture prior to polymerisation. The reaction mixture thus has a homogenous structure containing both hydrophilic and hydrophobic components that are intimately mixed, as the NNDMA acts as a solvent for both hydrophilic and hydrophobic materials, providing a clear compatible coating solution or dispersion. As the reactive solvent bridge is polymerised and thus essentially removed from the reaction mixture the stability of the system is adversely affected and the compatible coating solutions or dispersions undergo phase separation so as to provide a biphasic structure.

In certain circumstances the reaction mixture preferably comprises from 3% to 20%, and more preferably from 8% to 18% by weight of the reaction mixture, of a stabilised polymer dispersion that is used to provide a stable phase separated system. The polymer preferably comprises any of the following either alone or in combination: vinylacetate dioctyl maleate copolymer or ethylene-vinyl acetate copolymer. Ethylene-vinylacetate copolymer is preferred, such as that marketed under the trade name DM137 by Harlow Chemicals.

The adhesive is thus typically formed by polymerising an aqueous reaction comprising from 5 to 50%, preferably from 30% to 50% by weight of the reaction mixture, of hydrophilic monomer, i.e. an ionic water soluble monomer, from 10% to 50%, preferably from 15% to 45% by weight of the reaction mixture, of a plasticiser (other than water), from 10% to 50%, preferably from 15% to 30% more preferably from 15% to 25% by weight of the reaction mixture, of a hydrophobic nonionic monomer, i.e. nonionic water soluble monomer, from 3 to 40%, by weight of the reaction mixture, of water.

In preparing adhesive compositions in accordance with the invention, the ingredients will usually be mixed to provide a reaction mixture in the form of an initial pre-gel aqueous based liquid formulation, and this is then converted into a gel by a free radical polymerisation reaction. This may be achieved for example using conventional thermal initiators and/or photoinitiators or by ionizing radiation. Photo-initiation is a preferred method and will usually be applied by subjecting the pre-gel reaction mixture containing an appropriate photoinitiation agent to UV light after it has been spread or coated as a layer on siliconised release paper or other solid substrate. The incident UV intensity, at a wavelength in the range from 240 to 420 nm, is ideally substantially 40 mW/cm$^2$. The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers and for conversion better than 99.95% exposure to UV light less than 60 seconds and preferably less than 40 seconds is preferred. Those skilled in the art will appreciate that the extent of irradiation will be dependent on the thickness of the reaction mixture, concentration of photoinitiator and nature of substrate on to which the reaction mixture is coated and the source of UV.

These timings are for medium pressure mercury arc lamps as the source of UV operating at 100 W/cm. The intensity of UV @ 254 nm and 313 nm reaching the surface of the substrate is approximately 150 $\mu$W/cm$^2$ and 750 $\mu$W/cm$^2$. For a given lamp UV intensity in a function of the operating power and distance of the reaction mixture from the UV source.

In order to minimize and preferably eliminate the presence of any residual monomers it is important to ensure that the reaction is complete. This is dependent upon a number of factors such as the substrate onto which the adhesive is applied, the type and intensity of the ultra violet light and the number of ultra violet light passes. Preferably the conversion of the hydrophilic monomers present such as NaAMPS should be 98%, preferably 99.0% most preferably 99.9% so that the amount of monomer within the adhesive is 4600 microg/g or less, preferably 2300 microg/g or less, most preferably 230 microg/g or less. Similarly, the conversion of the hydrophobic monomers present such as NNDMA should be 99%, preferably 99.9%, most preferably 99.99% so that the amount of monomer present in the adhesive is 2200 microg/g or less, preferably 220 microg/g or less, most preferably 22 microg/g or less.

The adhesive is provided, typically on at least a portion of the wearer facing surface of the article, as a layer having a thickness or calliper C that is preferably constant, or that alternatively can vary over the surface of application of the adhesive.

When considering particularly the removal phase of an adhesive composition for attachment to the skin of a wearer, it is commonly recognised that good conditions of removal, i.e. at a frequency of about 100 rad/sec, of the adhesive applied to at least part of the wearer facing surface of the article, are achieved when the adhesive can be easily removed from the skin, and particularly from the bodily hair that may be located on this area of the skin, where the article contacts the body, without causing pain to the wearer, therefore without adhering too hard upon removal, to the skin and the hair of the wearer. Moreover, a good removal implies that the adhesive does not leave residues on the skin or on the hair. The relationship between the thickness or calliper C measured in millimeters (mm) of the layer of the adhesive typically onto at least part of the wearer's facing surface of the absorbent article and the viscous modulus $G''_{25}$ at 25° C. at about 100 rad/sec of the adhesive gives an indication of painless and easy removal of the adhesive from the skin.

Without being bound to any theory, it is believed that for higher values of $G''_{25}$ at 100 rad/sec, which overall correspond to a higher adhesiveness of the composition, a thicker calliper or thickness C of the adhesive layer is needed so that the energy applied for the removal is more evenly distributed within the mass of the adhesive, and is therefore transferred smoothly to the skin, so avoiding peaks of energy that typically cause the pain sensation to the wearer. In other words, thinner layers of the adhesive necessitate an adhesive with a lower $G''_{25}$ at 100 rad/sec to achieve a reduced pain sensation upon removal of the article.

According to the present invention, the adhesive is preferably provided as a layer having a thickness C such that the viscous modulus $G''_{25}$ (100 rad/sec) and the thickness C of the adhesive layer satisfy the following empirical equation:

$$G''_{25} \leq [(7.00+C) \times 3000] Pa$$

and preferably the following empirical equation:

$$G''_{25} \leq [(5.50+C) \times 1700] Pa$$

While in a preferred embodiment of the present invention the thickness C of the adhesive layer is constant, such an adhesive layer can also have different thicknesses in different portions of the wearer facing surface where it is applied, provided that the above mentioned relationship between C and $G''_{25}$ is in any case satisfied in each portion.

In order to evaluate the effect of the thickness C of the adhesive layer in its relationship with the viscous modulus $G''_{25}$ (100 rad/sec) of the adhesive of the present invention on the removal of the adhesive used for the attachment of a article to the skin of a wearer, a Removal Pain Grade Test has been developed. In this test the adhesion of standard substrates, on which the same adhesive has been provided in layers having different thicknesses, on the skin of the forearm of members of a sensory panel is achieved, and upon successive removal the pain is evaluated in terms of pain grade as described herein after.

Description of the Disposable Absorbent Article

Absorbent articles in which the adhesive according to the present invention can be used, can be made by any of the ways usual in the art. The application of the adhesive to the wearer facing surface, typically the topsheet surface of an absorbent article should not cause major problems to those skilled in the art since it can be provided by any well known techniques commonly used to apply adhesives. Most preferably the adhesive is provided in a pattern of small incremental areas such as dots or similar.

The adhesive is applied on at least portion of the wearer facing surface of disposable absorbent articles in a layer having a thickness or caliper that is preferably constant, or that alternatively can vary over the surface interested by the application of the adhesive. The adhesive can be applied to the wearer facing surface of the article by any means known in the art such as slot coating, spiral or bead application or printing. Typically the adhesive is applied at a basis weight of from 20 g/m$^2$ to 2500 g/m$^2$, preferably from 500 g/m$^2$ to 2000 g/m$^2$, most preferably from 700 g/m$^2$ to 1500 g/m$^2$ depending in the end use envisioned.

If possible, the article also provides breathability by being at least water vapour permeable, preferably air permeable to prevent stuffiness. Breathability, if not supported by the adhesive as such, can be limited to the area of the article where no adhesive is applied.

The adhesive on an article is preferably protected prior to use. This protection can be provided by a release liner such as a siliconised or surfactant treated paper, providing easy release for the selected adhesive.

This invention can be used beneficially on disposable absorbent articles which are applied directly to the skin of a user. The article usually exhibits absorbency for bodily fluids, the protection of the user's garments from soiling, is comfortable to the user, and is easy to produce and to package. The disposable absorbent article is described below by reference to a sanitary napkin or catamenial, however diapers, panty liners, adult incontinence articles, tampons or perspiration pads are also included under the term disposable absorbent articles. The term "sanitary napkin", as used herein, refers to an article which is worn by females adjacent to the pudendal region and which is intended to absorb and contain the various body fluids which are discharged from the body (e.g., vaginal discharges, menses, and/or urine) and which is intended to be discarded after a single use. A disposable absorbent article is preferably thin, more preferably between 1 and 5 mm thick and either substantially flat prior to use or in a preshaped form.

The terms "joined" or "affixed", as used herein, encompasses configurations whereby a first member is directly connected to a second member and configurations whereby a first member is indirectly connected to a second member by connecting the first member to intermediate members which in turn are connected to the second member.

The sanitary napkin has two main surfaces, a body contacting or wearer facing surface on which the adhesive is applied and a garment facing or contacting surface. In a one preferred embodiment a sanitary napkin of the present invention comprises a liquid pervious topsheet, a liquid impervious backsheet joined to the topsheet, and an absorbent core intermediate the topsheet and the backsheet. In an alternative embodiment, the sanitary napkin or panty liner may utilize the adhesive to absorb quantities of liquid up to amounts of about 10 g, such that a separate core and topsheet are not required. Such products preferably have a backsheet as described below.

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness.

Preferred topsheets for use in the present invention are typically selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the wearer remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred micro apertured formed film topsheets are disclosed in U.S. Pat. Nos. 4,609,518 and 4,629,643. A preferred topsheet for the present invention comprises the formed film described in one or more of the above patents and marketed on sanitary napkins by The Procter & Gamble Company of Cincinnati, Ohio as "DRI-WEAVE".

Adhesives are most suitably used on topsheets having not a homogeneous distribution of liquid passage ways but only a portion of the topsheet comprising liquid passage ways oriented such that they result in a centrally permeable and peripherally impermeable topsheet for liquids.

Another alternative are so called hybrid topsheets which incorporate fibrous and film like structures particularly useful embodiments of such hybrid topsheets are disclosed in PCT publications WO 93/09744; WO 93/11725 or WO 93/11726.

When referring to the topsheet a multi layer structure or a mono layer structure is contemplated. The hybrid topsheet mentioned above is such a multi layer design but other multi layer topsheets such as primary and secondary topsheet designs are also considered.

The absorbent core also can comprise multiple layers and provides fluid storage and distribution function.

Positioned in fluid communication with, and typically underlying the topsheet is the absorbent core. The core can comprise any usual absorbent material or combinations thereof. It preferably comprises absorbent gelling materials usually referred to as "hydrogel", "superabsorbent", "hydrocolloid" materials in combination with suitable carriers.

Suitable absorbent gelling materials for use herein will most often comprise a substantially water-insoluble, slightly cross-linked, partially neutralised, polymeric gelling material. This material forms a hydrogel upon contact with water. Such polymer materials can be prepared form polymerizable, unsaturated, acid-containing monomers, such as acrylic acid, which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins/panty liners.

An embodiment of the core, particularly useful in the application of the present invention, comprises a double layer tissue laminate formed by folding the tissue onto itself. These layers can be joined to each other. Absorbent gelling material or other optional material can be comprised between the layers.

The absorbent core can include optional components normally present in absorbent webs such as odor control agents, in particular suitable zeolites.

The backsheet primarily prevents the exudates absorbed and contained in the absorbent core from wetting articles that contact the absorbent product such as underpants, pants, pyjamas and undergarments. The backsheet is preferably impervious to liquids (e.g. menses and/or urine) and usually manufactured from a thin plastic film.

The backsheet typically extends across the whole of the absorbent core and can extend onto and form part of the topsheet by folding around the absorbent core. Thereby a topsheet configuration as disclosed in U.S. Pat. No. 4,342, 314, column 16, lines 47–62 can be achieved without the requirement to selectively aperture the topsheet.

Preferably, the backsheet also provides breathability to the absorbent article by being at least water vapour permeable, preferably air permeable. The backsheet can be a laminate material e.g. of a combination of microporous film and/or non-woven material, and/or apertured formed film. Breathability if desired can be limited to the periphery or the center of the backsheet or it can be across the whole backsheet.

According to the present invention the adhesive as described herein may also find application to attach other articles to the skin. The adhesives may for example find utility to adhere functional articles which adhere to the skin such as cosmetic or pharmaceutical delivery articles which provide a substance to the skin such as skin treatment substances, cream, lotions, hormones, vitamins, deodorants, drugs; cosmetic or pharmaceutical delivery articles provide a substance to emanate away from the skin such as insecticides, inhalation drugs, perfumes and; functional articles which are not necessarily attached to the skin, but which require a high residence time on the skin such as decorative cosmetics, (lipstick, eye shadow, stage make-up) and cleaning articles (hand cleaners, face masks and hygienic pore cleansers). Such articles are preferably non-absorbent for bodily liquids.

The adhesive may also in addition find application to attach articles to the skin such as protective articles such as genital-, knee- or elbow-protectors or bandages; clothing such as bras, surgical gowns, or parts of garments during fitting at a tailor; nasal plasters; prosthesis such as breast replacements or wigs; cold wraps e.g. to provide pain relief from bruises and to reduce swelling; thermal wraps comprising thermal cells as disclosed for example in WO97/36968 and WO97/493 61 to provide relief of temporary and chronic pain such as neck wraps as disclosed in for example U.S. Pat. No. 5,728,146, knee wraps exemplified in WO97/01311, and back wraps as disclosed for example in U.S. Pat. No. 5,741,318; hearing aids; protective face masks (for the reduction or prevention of inhalation of noxious substances); ornamental articles such as jewelry, earrings, guises, tattoos; goggles or other eye wear; ostomy devices, tapes, bandages, dressings of general utility, wound healing and wound management devices; and biomedical skin electrodes such as ECG, EMG, EEG, TENS electrosurgery, defibrillation, EMS and electrodes for facial/beauty applications; and fixation products and/or devices intended to affix patient catheters, tubing leadwires cables etc.

Removal Pain Grade Test

The Removal Pain Grade Test is utilized to evaluate the pain during removal from the skin of a wearer of a sample provided with a layer of a adhesive and previously attached to the wearer's skin. The test specifically evaluates the pain upon removal of each sample as compared to the pain obtained by removing a reference sample constituted by a commercial strong medical plaster.

Sample Preparation.

The test is performed on rectangular samples 60×20 mm made of a polyester film 23 μm thick, such as that sold by Effegidi S.p.A. of Colorno (Parma, Italy), provided on one side with a continuous layer of the adhesive having the selected thickness. The reference sample is a 60×20 mm sample of an adhesive non woven fabric available from Beiersdorf A. G. Hamburg, Germany under the Tradename Fixomull stretch.

Test Method.

A panel of six graders is selected for the test. The test is performed in a climatically controlled laboratory maintained at a temperature of 23° C. and a Relative Humidity of 50%. No special treatment of the wearer's skin is required beyond normal cleaning/washing with water and soap. The skin is then allowed to dry for at least two hours before the test to allow the skin to reach equilibrium with the room conditions. Different adhesive are evaluated in the test in comparison with the reference sample R. Each sample is applied by hand by an operator to the inner part of the grader's forearm, being centred between the wrist and the elbow, with the short side of the sample aligned with the length of the arm. The operator exerts on each sample with the palm of the hand the same pressure that is typically applied to cause a medical plaster to adhere to the skin. Each sample is worn for the prescribed time, and then it is removed from the grader's skin by the operator with a slow and smooth pull.

Four series of one reference sample R and the test samples are each applied, worn and then removed from the wearer's skin; each sample is worn for one minute, with a 5 minute wait between two subsequent samples of the same series, and a 15 minute wait between two different subsequent series. The reference sample R is always applied, worn and removed as the first sample of its respective series. The sequence of application/wear/removal of the test samples in each of the first three series is random, provided that no repetition in each series is allowed, and that no sequence is repeated in the first three series. In the fourth series one of the test samples is tested twice, the reference R always being the first one. Overall each sample has to be tested an equal number of times (24 times).

The graders were asked to evaluate each sample using a pain scale ranging from 0 to 10, where 0 corresponds to no pain and 10 corresponds to the pain upon removal of the reference sample R. The pain values for each sample were obtained as a mean of 24 observations.

The results collected from the test were analysed by a statistical analysis program "Comparison of Population Means—Paired Samples", that showed that the differences between the pain values of the samples are statistically significant.

Peel Adhesion Method

This is a quantitative method to determine the average peel force required to remove a skin at a specified peel angle and speed.

Equipment

| | |
|---|---|
| Scissors | Convenient source |
| Standard ruler | Convenient source |
| Steel Roller | 5.0 kg Mass. 13 cm in diameter and 4.5 cm in width covered with 0.5 mm thick rubber. |
| Polyester Film | PET 23 μ available from EFFEGIDI S.p.A., 43052 Colorno, Italy. |
| Transfer Adhesive | 3M 1524 available from 3M Italia S.p.a., 20090 Segrate Italy |
| Stop watch | Convenient source |
| Tensile Tester | Instron mod.: 6021 (or equivalent) |

Test Procedure

A) Tensil Tester Settings:

| | |
|---|---|
| Load cell | 10N |
| Test Speed | 1000 mm/min |
| Clamp to Clamp distance | 25 mm |
| Pre Loading | 0.2N |
| Test Path "LM" | 50 mm |
| Measure variable | F average (N) in "LM" |

B) Skin Condition and Preparation

The sample is peel from the forearm. There are 3 conditions of the skin that are tested:

1) Dry: The forearm is untreated and not wiped prior to test or between repetitions.
2) Wet: To one cotton disk (Demak'up diameter 5.5 cm, weight about 0.6 g), 3 ml of distilled water is added.

Next the disk is then wiped with a light pressure 3 times over the test area on the forearm. (The test area of the forearm is a rectangle approximately 2 cm wider and longer than the adhesive area).

C) Sample Preparation

1. Allow the samples to adjust to conditioned room (23 ±2° Celsius and 50±2% RH) for about 1 hr.
2. Prepare rectangular adhesive samples 260 mm ±2 length and 20 mm ±2 wide.
3. Attach on the sample surface the polyester film (using the transfer adhesive to attach the polyester to the substrate surface).
4. Each test specimen should be prepared individually and tested immediately.
5. Remove the release paper from the adhesive without touching it. Attach one end to the skin (see section B).
6. Roll the Steel Roller for 160 mm along the adhesive strip, once in each direction.

D) Test Environment

There are 2 environments the adhesive can be tested in:
1) Conditioned Room as described in C1.
2) Wet Environment. Here, after step C4, the specimen is taken and put in a humidity controlled oven for 3 hours at 85 degC. It is then taken out and steps C5, C6 are carried out.

E) Execution 1 minute after Step C6, take the free end of the specimen (approx. 100 mm long) and insert it in the upper end of the adhesion testing machine. Ensure the specimen is at a 90 degree angle to the forearm. Start the testing machine.

F) Report

Report the average of the peel strength of 5 tests. The single values are the base to calculate the standard deviation between the samples.

Residual Monomer Test Method

Test Sample 1 gram of a hydrogel sample is taken and emersed in 100 ml 0.9% saline water.

The sample is left in the saline at 40 degC for 24 hours.

An aliquot of the liquid is diluted and analysed by electrospray LC/MS/MS.

Calibration Sample 1 gram of reference monomers (eg NaAmps) are dissolved in 100 ml 0.9% saline water.

An aliquot of the liquid is diluted and analysed by electrospray LC/MS/MS.

Evaluation

The concentration of the test and calibration sample are determined by linear regression analysis using a software package such as VG Mass Lynx.

Adhesive Preparation

The following is the general description to prepare 20 kg of the adhesive at room temperature and pressure. 250 ml of triethanolamine is placed in a 80 l plastic beaker and stirred. N,N,-dimethylacrylate (NNDMA) is added to the beaker and stirred. Glycerol is then added and the entire mixture is stirred for 5 minutes. Sodium 2 acrylamide 2 methyl propane sulphonic acid (NaAMPS) is then added and the mixture stirred for 5 minutes. The crosslinker is then added and the mixture is again stirred for at least 30 minutes. The mixture is then extruded onto a substrate material prior to UV curing. The UV curing consists of 2–4 passes under a bank of 3 UV lights.

The reference material is prepared as above, except that the NNDMA is replaced by acrylic (3 sulphopropyl) ester acid SPA and the mixture is stirred for 24 hrs. at 53° C. prior to UV curing.

All formulations detailed below were coated onto a polyurethane foam (EV 1700X from Caligen) at a coat weight of 0.8 to 1.6 kg per square meter and cured by expose to ultraviolet radiation emitted from a medium pressure mercury are lamp operating at 100 w/cm power for 10 seconds.

| | Results | | | |
|---|---|---|---|---|
| Component | Reference | 1 | 2 | 3 |
| NaAMPS (58%) | 37 | 40 | 32.5 | 32.5 |
| NNDMA | — | 23.5 | 18 | 18 |
| Glycerol | 33 | 30 | 45 | 40 |
| SPA | 15 | — | — | — |
| Vinyl acetate | 10 | — | — | — |
| Photoinitiator | 0.03 | 0.07 | 0.23 | 0.23 |
| Crosslinker | 0.11 | 0.13 | 0.05 | 0.07 |
| No. of UV passes | 4 | 1 | 3 | 3 |
| $P_I$ (N/cm) | 2.5 | 2.55 | 2.70 | 0.95 |
| $P_F$ (N/cm) | 1.43 | 2.10 | 2.70 | 1.81 |
| P (Water absorbency of 20%, N/cm) | 0.43 | — | 1.88 | 1.13 |
| $G'_{37}$ (dynes/cm$^2$) | 90712 | 187680 | 171330 | 181340 |
| $G''_{37}$ (dynes/cm$^2$) | 59338 | 104750 | 119400 | 124660 |

What is claimed is:

1. An adhesive for a disposable absorbent article:

said disposable absorbent article comprising a wearer facing surface and a garment facing surface opposed thereto;

said adhesive covering at least a portion of said wearer facing surface;

said adhesive having an initial peel strength ($P_I$);

wherein said adhesive has a final peel strength ($P_F$) after exposure to water;

wherein the ratio of $P_I$ to $P_F$ is in the range of 2:1 to 2:4;

wherein said adhesive comprises at least one non-emulsified homogeneous phase or at least one emulsified phase wherein all of said phases have a thickness greater than 50 µm;

wherein said adhesive has a water absorption capacity of at least 3% by weight of said adhesive; and, wherein said adhesive comprises at least 3% water after one hour of equilibration at 50% relative humidity.

2. The adhesive of claim 1, wherein said ratio of $P_I$ to $P_F$ ranges from 2:1.25 to 2:2.

3. The adhesive of claim 1, wherein said initial peel strength ($P_I$) of said adhesive ranges from 0.1N/cm to 5.0N/cm.

4. The adhesive of claim 3, wherein said initial peel strength ($P_I$) of said adhesive ranges from 0.5N/cm to 3.0N/cm.

5. The adhesive of claim 1, wherein:

said adhesive is provided as a layer having a thickness C in millimeters;

wherein said adhesive has a viscous modulus at a temperature of 25° C. ($G''_{25}$(100 rad/sec)); and, wherein said viscous modulus ($G''_{25}$(100 rad/sec)) is defined by the equation:

$$G''_{25} \leq [(7.00+C) \times 3000] \text{ Pa.}$$

6. The adhesive of claim 5, wherein:

said viscous modulus ($G''_{25}$(100 rad/sec)) is defined by the equation:

$$G''_{25} \leq [(5.50+C) \times 1700] \text{ Pa.}$$

7. The adhesive of claim 1, wherein:

said adhesive has an elastic modulus at a temperature of 37° C. ($G'_{37}$(1 rad/sec)) and a viscous modulus at a temperature of 37° C. ($G''_{37}$(1 rad/sec));

wherein $G'_{37}$(1 rad/sec) ranges from 500 Pa to 20000 Pa;

wherein $G''_{37}$(1 rad/sec) ranges from 100 Pa to 15000 Pa; and, wherein the ratio $G'_{37}$(1 rad/sec)/$G''_{37}$(1 rad/sec) ranges from 1 to 30.

8. The adhesive of claim 7 wherein:

$G'_{37}$(1 rad/sec) ranges from 700 Pa to 15000 Pa; and, wherein $G''_{37}$(1 rad/sec) ranges from 100 Pa to 10000 Pa.

9. The adhesive of claim 8 wherein:

$G'_{37}$(1 rad/sec) ranges from 1000 Pa to 10000 Pa; and, wherein $G''_{37}$(1 rad/sec) range from 300 Pa to 5000 Pa.

10. The adhesive of claim 1, wherein said adhesive is a substantially water insoluble pressure sensitive adhesive comprising a polymer which forms a 3-dimensional matrix, and comprises less than 10% hydrocolloid particles by weight of said adhesive.

11. The adhesive of claim 10, wherein said adhesive comprises less than 5% hydrocolloid particles by weight of said adhesive.

12. The adhesive of claim 1, wherein said adhesive comprises:

a polymer selected from the group consisting of polyacrylics, sulphonated polymers, polyvinyl alcohols, polyvinyl pyrrolidine, polyethylene oxide, and mixtures thereof; and, a plasticizer selected from the group consisting of polyhydric alcohols, polyethylene glycols, sorbitol, water, and mixtures thereof.

13. The adhesive of claim 12, wherein said adhesive is a hydrophilic-hydrophobic mixed phase adhesive.

14. The adhesive of claim 1, wherein said wearer facing surface further comprises at least one non-adhesive portion.

15. The adhesive of claim 1, wherein said adhesive is a continuous layer.

16. The adhesive of claim 1, wherein said adhesive is applied to said wearer facing surface by slot coating.

17. The adhesive of claim 1, wherein said article further comprises a release liner in contact with said adhesive.

18. The adhesive of claim 1, wherein said article further comprises a topsheet in communication with said garment facing surface, a backsheet in communication with said topsheet, and an absorbent core disposed therebetween.

19. The adhesive of claim 1, wherein said adhesive is applied to said wearing facing surface at a basis weight ranging from 20 g/m² to 2500 g/m².

20. The adhesive of claim 19, wherein said adhesive is applied to said wearing facing surface at a basis weight ranging from 700 g/m² to 1500 g/m².

21. The adhesive of claim 1, wherein said adhesive is formed by polymerizing a homogeneous aqueous reaction mixture comprising from 5% to 50% by weight of the reaction mixture of a hydrophilic monomer from 10% to 50% by weight of the reaction mixture of a plasticizer, and from 10% to 50% by weight of the reaction mixture of a non-ionic monomer, and from 3% to 40% by weight of the reaction mixture of water.

* * * * *

UNITED STATES PATENT AND TRADEMARK OFFICE
CERTIFICATE OF CORRECTION

PATENT NO. : 6,710,099 B2
DATED : March 23, 2004
INVENTOR(S) : Cinelli et al.

It is certified that error appears in the above-identified patent and that said Letters Patent is hereby corrected as shown below:

<u>Title page,</u>
Item [*] Notice, should read: -- Subject to any disclaimer, the term of this patent is extended or adjusted under 35 U.S.C. §154(b) by 29 days.

This patent is subject to a terminal disclaimer. --

Signed and Sealed this

Nineteenth Day of April, 2005

JON W. DUDAS
*Director of the United States Patent and Trademark Office*